(12) United States Patent
Kierulff

(10) Patent No.: US 6,346,401 B1
(45) Date of Patent: Feb. 12, 2002

(54) MODIFICATION OF POLYSACCHARIDES BY MEANS OF A PHENOL OXIDIZING ENZYME

(75) Inventor: Jesper Vallentin Kierulff, Roskilde (DK)

(73) Assignee: Novozymes A/S, Bagsvaerd (DK)

(*) Notice: Subject to any disclaimer, the term of this patent is extended or adjusted under 35 U.S.C. 154(b) by 0 days.

(21) Appl. No.: 09/320,514

(22) Filed: May 26, 1999

Related U.S. Application Data

(62) Division of application No. 09/221,009, filed as application No. PCT/DK98/00563 on Dec. 18, 1998, now Pat. No. 6,087,135.
(60) Provisional application No. 60/068,647, filed on Dec. 23, 1997.

(30) Foreign Application Priority Data

Dec. 19, 1997 (DK) .......................... 1997 01491

(51) Int. Cl.$^7$ .......................... C12P 19/04; C12P 19/00; C12P 7/44; C12N 19/04
(52) U.S. Cl. .......................... 435/101; 435/72; 435/136; 435/142; 435/189; 435/190
(58) Field of Search .......................... 435/101, 72, 136, 435/142, 189, 190

(56) References Cited

U.S. PATENT DOCUMENTS 6,087,135 A * 7/2000 Kierulff ...................... 435/101

FOREIGN PATENT DOCUMENTS

| CA | 2164394 | * | 6/1996 |
|----|---------|---|--------|
| WO | WO 91/05839 | | 5/1991 |
| WO | WO 93/10158 | | 5/1993 |
| WO | WO 96/03440 | | 2/1996 |
| WO | WO 96/18770 | | 6/1996 |
| WO | WO 97/25468 | | 7/1997 |

OTHER PUBLICATIONS

Dialog Info. Services, File 34, SciSearch, Accession No. 03742053.

Hebeish et al., (1994) Cellulose Chem. And Tech. 28:409–418.

Varma et al., (1995) Elsevier 49:245–250.

Abdel–Hafiz (1997) Elsevier 55:9–16.

Santacesaria et al., (1994) Elsevier 23:35–46.

* cited by examiner

Primary Examiner—Francisco Prats
(74) Attorney, Agent, or Firm—Elias J. Lambiris, Esq.; Jason I. Garbell, Esq.

(57) ABSTRACT

The present invention deals with a process for oxidation of a hydroxy group of $C_1$ and/or $C_2$ and/or $C_3$ and/or $C_4$ and/or $C_5$ and/or $C_6$ of a sugar monomer of an oligo- or a polysaccharide comprising contacting, in an aqueous medium, the oligo- or the polysaccharide with a phenol oxidizing enzyme and an enhancing agent, whereby an oligo- or a polysaccharide with altered characteristics compared to the native oligo- or polysaccharide is created.

11 Claims, 2 Drawing Sheets

MODIFICATION OF POLYSACCHARIDES BY MEANS OF A PHENOL OXIDIZING ENZYME

CROSS-REFERENCE TO RELATED APPLICATIONS

This application is a divisional of U.S. application Ser. No. 09/221,009 filed Dec. 23, 1998, now U.S. Pat. No. 6,087,135, which is a continuation of PCT/DK98/00563 filed Dec. 18, 1998 and claims priority under 35 U.S.C. 119 of Danish application PA 1997 01491 filed Dec. 19, 1997 and U.S. provisional application Serial No. 60/068,647 filed Dec. 23, 1997, the contents of which are fully incorporated herein by reference.

FIELD OF INVENTION

The present invention relates to a process for enzymatic oxidation of soluble as well as insoluble oligo- or polysaccharides such as starch and cellulose wherein the oligo- or polysaccharide is oxidized introducing carbonyl groups and/or carboxylate groups giving products with improved functional properties.

BACKGROUND ART

Oxidation of polysaccharides by various chemicals are known in the art:

Oxidation of cellulose, for example, causes changes in the structure and crystallinity of the resulting molecule, which affects its chemical and physical properties. Varma and Chavan [Varma, A. J., and Chavan, V. B. (1995), Polymer Degradation and Stability, 49, pp 245–250] found a proportionality between the decrease in degree of crystallinity and increase in degree of oxidation. Further, Varma and Chavan from cellulose created sodium 2,3-dicarboxy cellulose by oxidizing cellulose to 2,3-dialdehyde cellulose by periodate oxidation followed by oxidation of the 2,3-di-aldehyde cellulose to 2,3-di-carboxy cellulose by sodium chlorite. The 98% sodium 2,3-dicarboxy cellulose was found to be water soluble.

Further, oxidized polyglucosides have interesting properties as calcium sequestrants and are useful as tripolyphosphate substitutes in detergent formulation [Santacesaria, E., Trulli, F., Brussani, G. F., Gelosa, D., and Di Serio, M. (1994), Carbohydrate Polymers, 23, pp 35–46].

Further, various kinds of polysaccharides, in particular starch, are of utmost importance as a sizing agent in the textile industry, in addition to application as a processing aid in printing and finishing. However, the properties of the native starch is not always optimal compared to the properties required for the particular application. One of the problems of native starch is the very large molecular size, the insolubility, the instability of viscous solutions under varying temperature, and its susceptibility to microbial degradation. Consequently, chemical modification of starches has become an important tool to overcome the problems and create starches having altered characteristics compared to the native starch. Common treatments involve acid treatment, oxidation, etherification, esterification, grafting, and preparation of poly (vinyl)-starch composites [Abdel-Hafiz, S. A. (1997), Polymer Degradation and Stability, 55, pp 9–16].

In addition, Hebeish et al. [Hebeish, A., El-Kashouti, M. A., Abdel-Thalouth, I., Haggag, K., and El-Halwagi, A. (1994), Cellulose Chemistry and Technology, 28, pp 409–418] have shown, that the degree of substitution when Carboxy Methyl Cellulose (CMC) is produced depends on the degree of oxidation of the cellulose base-material, and various qualities of CMC can thus be produced using cellulose with varying degrees of oxidation.

There is thus an increasing interest in and need for methods capable of introducing oxidative changes of various kinds in oligo- and polysaccharides.

SUMMARY OF THE INVENTION

The present invention relates to a process for oxidation of a hydroxy group of $C_1$ and/or $C_2$ and/or $C_3$ and/or $C_4$ and/or $C_5$ and/or $C_6$ of a sugar monomer of an oligo- or a polysaccharide comprising contacting, in an aqueous medium, the oligo- or the polysaccharide with a phenol oxidizing enzyme, together with a hydrogen peroxide source when the phenol oxidizing enzyme is a peroxidase, and an enhancing agent, whereby an oligo- or a polysaccharide with altered characteristics compared to the native oligo- or polysaccharide is created.

BRIEF DESCRIPTION OF THE DRAWINGS

The present invention is further illustrated by reference to the accompanying drawings, in which.

DETAILED DESCRIPTION OF THE INVENTION

It is the purpose of the present invention to create an enzymatic oxidative modification of oligo- or polysaccharides whereby new functional groups are produced.

Accordingly, we have created a process for oxidation of a hydroxy group of $C_1$ and/or $C_2$ and/or $C_3$ and/or $C_4$ and/or $C_5$, and/or $C_6$ of a sugar monomer of an oligo- or a polysaccharide comprising contacting, in an aqueous medium, the oligo- or the polysaccharide with a phenol oxidizing enzyme, together with a hydrogen peroxide source when the phenol oxidizing enzyme is a peroxidase, and an enhancing agent, whereby an oligo- or a polysaccharide with- altered characteristics compared to the native oligo- or polysaccharide is created.

In particular we have created a process for oxidation of a hydroxy group of $C_2$ and/or $C_3$ and/or $C_6$ of a sugar monomer of an oligo- or a polysaccharide comprising contacting, in an aqueous medium, the oligo- or the polysaccharide with a phenol oxidizing enzyme, together with a hydrogen peroxide source when the phenol oxidizing enzyme is a peroxidase, and an enhancing agent, whereby an oligo- or a polysaccharide with altered characteristics compared to the native oligo- or polysaccharide is created.

Especially, we have created a process for oxidation of a hydroxy group of $C_6$ of a sugar monomer of an oligo- or a polysaccharide comprising contacting, in an aqueous medium, the oligo- or the polysaccharide with a phenol oxidizing enzyme, together with a hydrogen peroxide source when the phenol oxidizing enzyme is a peroxidase, and an enhancing agent, whereby an oligo- or a polysaccharide with altered characteristics compared to the native oligo- or polysaccharide is created.

According to the present invention an oligosaccharide contains at least 20 monomers, preferably at least 50 monomers, in particular at least 100 monomers.

The oxidation according to the invention may result in creation of carbonyl groups (ketones and aldehydes) and/or carboxylate groups in the oligo- or polysaccharide resulting in an oligo- or a polysaccharide with altered characteristics compared to the native oligo- or polysaccharide.

Figure 1:
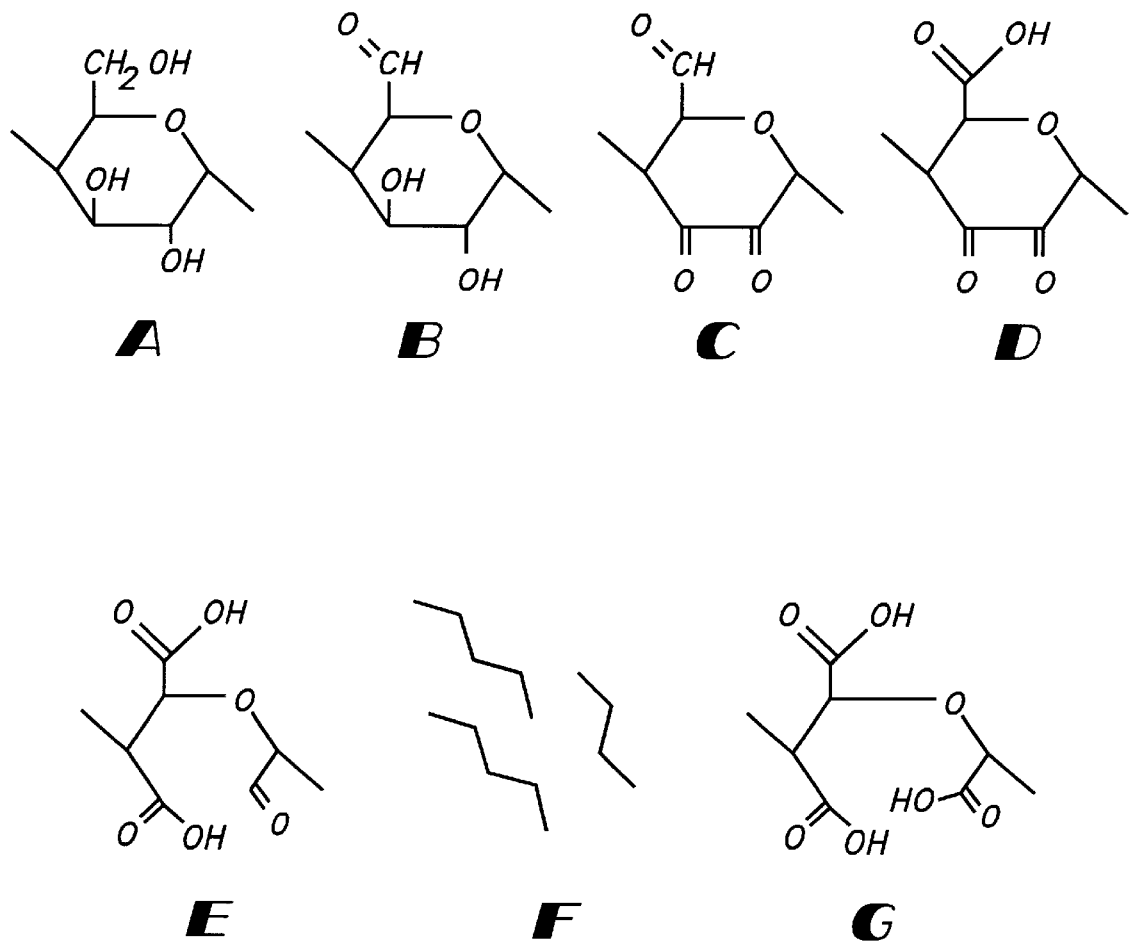
FIG. 1 illustrates an idealised model for the progressive oxidation of cotton cellulose.
Figure 2:
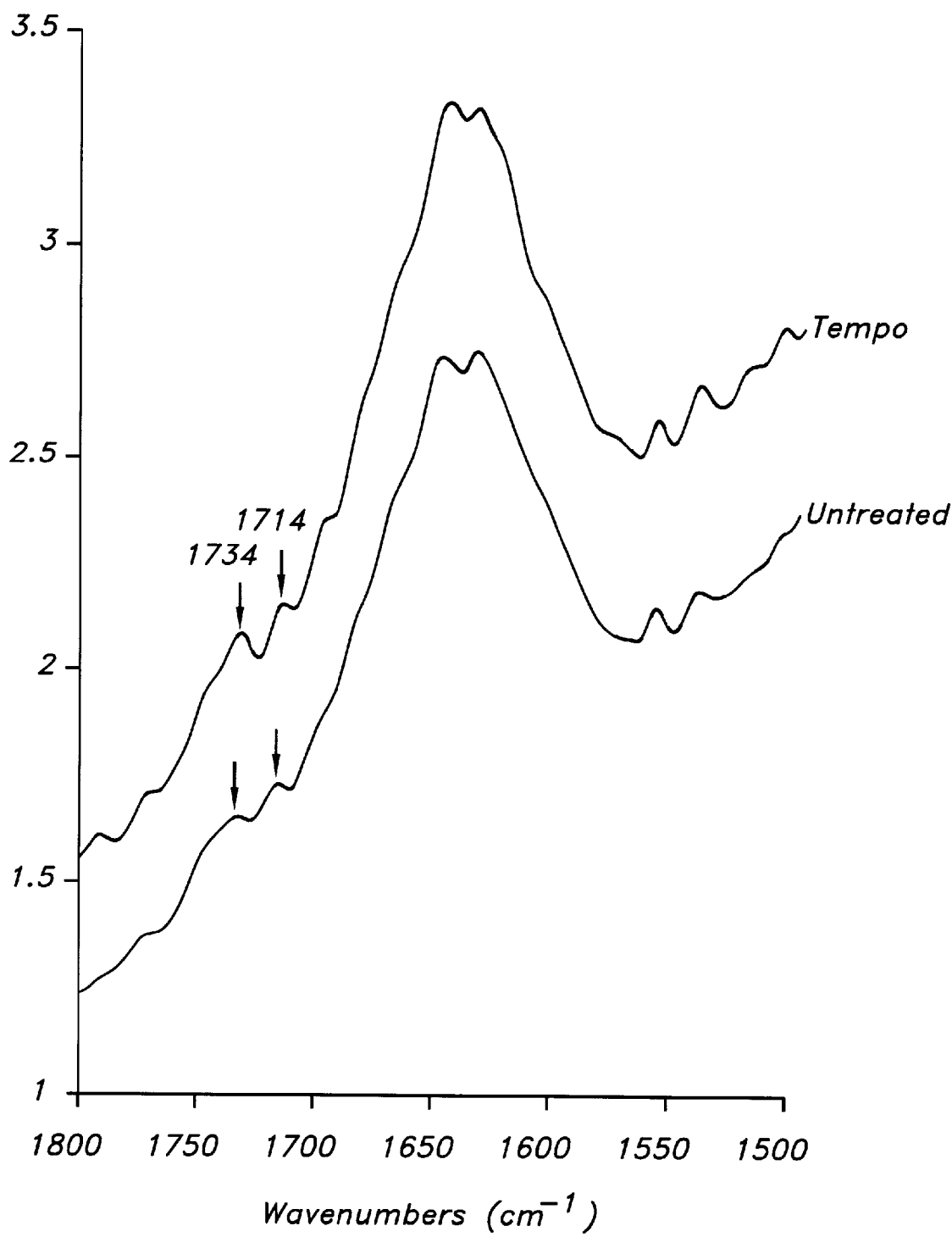
FIG. 2 shows FT-IR/PAS spectra of untreated white cotton as well as white cotton treated with Tempo/laccase covering the range 1800–1500 $cm^{-1}$ as described in Example 1.

An example of an idealised model for the progressive oxidation of cotton cellulose is illustrated in FIG. 1. This model demonstrates some of the types of changes to the cotton cellulose which might be expected with progressive oxidation. The number of carbonyl groups/carboxylate groups formed will increase with oxidation:

"A" illustrates unmodified glucose;

"B" illustrates carbonyl formation at $C_6$;

"C" illustrates carbonyl formation at $C_2$, $C_3$, and $C_6$;

"D" illustrates carbonyl formation at $C_2$ and at $C_3$, and carboxylate formation at $C_6$;

"E" illustrates carbonyl formation at $C_2$; carboxylate formation at $C_3$ and $C_6$; and ring opening;

"F" illustrates polymer scission and possible loss of material; and

"G" illustrates exposure and oxidation of new material.

Normally, the oxidation of interest will be the specific oxidation at $C_6$ (without or only a limited oxidation of the other C atoms) to carbonyl or carboxylate; and the enzymatically oxidation described in the present invention is particularly suited for such a specific and "delicate" oxidation.

The differences compared to the native oligo- or polysaccharide are the result of the oxidation as such, but the wanted differences will often be achieved by further modifications of the introduced changes in the oligo- or polysaccharide by other means such as chemically and/or enzymatically modifications.

For example new oligo- or polysaccharides, derived from e.g. cellulose, or composites/blends of naturally occurring oligo- or polysaccharides and artificial polymers, may be prepared for textile manufacture having altered surface charge, and/or altered dye ability and/or altered specificity for dyeing, and/or having new functional groups making covalent or non-covalent attachment and/or adsorption possible of compounds that are themselves containing or carrying other functional and thus valuable groups, making cross linking of polymer chains possible for creating wrinkle free fabric, durable press fabric, fabric with increased strength, water repellent fabric, flame retardant fabric, fabric with increased durable softness, dirt-repellent fabric, and/or anti-static appearance.

Methods for Examining Polysaccharide Oxidation

Two factors which give an indication of the degree of cotton oxidation are the formation of functional groups such as carbonyl groups and carboxylate, and the loss of fabric strength due to polymer scission or breakage. Thus, analysis of oxidation can either be done by measuring fabric tear strength, or by measuring the functional groups introduced.

Fabric tear strength test, commonly involving the measurement of the force required to propagate a tear in the fabric, can be used to provide an indication of fabric damage. However, several replicates are required to produce reasonable results and large variations can occur between replicates due to fibre defects [Cardamone, J. M., and Brown, P. (1986), Historic Textile and Paper, Ch. 3., ACS, Washington]. When considering relatively similar samples, the variation between replicates may exceed the variation between the samples, making comparison difficult. It must also be considered that mechanical damage to the fabric during processing will contribute to an overall fabric strength loss, so the tear strength measurements do not solely reflect oxidative damage.

Oxidation of cellulose initially results in the formation of carbonyl groups, with further oxidation resulting in the formation of carboxylic acids or carboxylate anions depending on the pH.

Staining methods for the determination of carboxylate and carbonyl groups have been extensively used to indicate the extent of oxidation in cotton fabrics. The application of the Tollen's reagent ($Ag(NH_3)_2OH$) to oxidized cotton results in black staining of all aldehyde groups due to precipitation of silver metal [Skoog, D. A., West, D. M., and Holler, F. J. (1992), Fundamentals of Analytical Chemistry, Ch. 20, Saunders College Publishers, Fl]. Other staining agents, such as 2,4-dinitrophenylhydrazine, can be used to identify both ketones and aldehydes. Relative ketone amounts can then be determined by subtraction. Methylene blue solutions can be used for the identification of carboxylate groups on cotton fabrics via the staining which results from the adsorption of methylene blue cations on the cellulose carboxylate groups [Lewin, M., and Sello, S. B. (Ed.) (1984), Chemical Processing of Fibres and Fabrics: Fundamentals and Preparation, part B, Marcel Dekker Inc. NY]. While staining methods are useful for indicating areas of oxidation, they can not provide quantitative measurements of oxidation without the preparation of an extensive standard series, and staining methods can not show specific oxidations. The staining methods are quite time-consuming and tedious, and extremely difficult to apply to dyed fabrics which are already coloured.

The measurement of carbonyl and carboxylate groups formed can also be achieved by the application of vibrational spectroscopy techniques such as Fourier Transform Infrared Spectroscopy (FTIR), Diffuse reflectance FTIR (DRIFT), and FTIR/Photoacoustic Spectroscopy (FTIR/PAS).

The infrared absorption band of most carbonyl groups on cotton-cellulose are observed in the 1700 to 1750 $cm^{-1}$ region of the spectrum, while cotton-cellulose carboxylate bands are typically observed in the 1550 to 1600 $cm^{-1}$ region, thus facilitating the measurement of oxidation by IR analysis [Cardamone, J. M, Gould, J. M., and Gordon, S. H. (1987), Text. Res. J., 57(4), pp 235–239, Yang, C. Q., and Fateley, W. G. (1990), Appl. Spectrosc., 44, pp 1035–1041, Yang, C. Q. (1991), Appl. Spectrosc., 45(1), pp 102–108].

Cardamone and Brown [Cardamone, J. M., and Brown, P. (1986), Historic Textile and Paper, Ch. 3., ACS, Washington] compared artificially and naturally aged cotton by measuring the integrated area of the 1540 to 1850 $cm^{-1}$ region of FTIR/PAS spectra, and illustrated the conditions which best replicate the naturally ageing process. Yang and various co-workers [Yang, C. Q., and Fateley, W. G. (1990), Appl. Spectrosc., 44, pp 1035–1041, Yang, C. Q. (1991), Appl. Spectrosc., 45(1), pp 102–108], have also carried out studies on the measurement of cotton oxidation using techniques such as DRIFTS, FTIR-PAS and Attenuated Total Reflectance. Comparison of the bulk material, from a ground cotton sample, and surface measurements carried out by Yang and Fateley [Yang, C. Q., and Fateley, W. G. (1990), Appl. Spectrosc., 44, pp 1035–1041] using FTIR/PAS illustrated that the oxidation of cotton fabrics is typically a surface feature and the evidence of oxidation is greatly reduced, if not removed, when studying the bulk sample.

The relative amounts of carbonyl and carboxylate groups can be used as an indication of cellulose oxidation and can be measured using vibrational spectroscopy. Near surface analysis of cotton fabrics using vibrational spectroscopy techniques such as DRIFTS and PAS has been successfully used to provide a measure of cellulose oxidation resulting from ageing and processing treatments [Cardamone, J. M, Gould, J. M., and Gordon, S. H. 1987), Text. Res. J., 57(4), pp 235–239, Kokot, S., and Jermini, M., (1994), Text. Res. J., 64(2), pp 100–105, Yang, C. Q., and Fateley, W. G. (1990), Appl. Spectrosc., 44, pp 1035–1041].

Kokot and various co-workers [Kokot, S., and Jermini, M., 1994), Text. Res. J., 64(2), pp 100–105, Kokot, S., Marahusin, L., Schweinsberg, D. P., and Jermini, M. (1994), Text. Res. J., 4(12), pp 710–716] also applied vibrational spectroscopy, in the form of DRIFTS, to the measurement of cotton oxidation. In this study, the spectra of a series of fabrics undergoing simulated bleaching processes were analysed using chemometric methods such as Principal Component Analysis and Partial Least Squares Regression. Using the wavenumber ranges 1750 $cm^{-1}$–1700 $cm^{-1}$ and 1575 $cm^{-1}$–1550 $cm^{-1}$, which is consistent with formation of carbonyl and carboxylate groups Kokot et al. separated cotton voile oxidized to different degrees from each other as well as from native cotton voile. This work highlighted the significance of the carbonyl and carboxylate spectral regions in the discrimination of cotton subjected to different levels of oxidation as well as the need for using multivariate analysis (chemometrics) in analysis of the spectral data.

The comparison of weathered and unweathered fabric by Yang and Fateley [Yang, C. Q., and Fateley, W. G. (1990), Appl. Spectrosc., 44, pp 1035–1041] highlighted absorption bands in the weathered fabric at 1722 and 1704 $cm^{-1}$. These bands were attributed to carbonyl absorption. Cardamone et al. [Cardamone, J. M, Gould, J. M., and Gordon, S. H. (1987), Text. Res. J., 57(4), pp 235–239] studied naturally and artificially aged cotton textiles to compare the extent of oxidative damage occurring under different environments. A measure of the extent of oxidation was obtained in the integrated area of the 1540 to 1850 $cm^{-1}$ range of the PA spectra. This research demonstrated the measurement of a selected spectral area to provide an indication of cellulose oxidation.

Kokot and Jermini [Kokot, S., and Jermini, M., (1994), Text. Res. J., 64(2), pp 100–105] used DRIFTS to characterise cotton fabrics that had been oxidatively damage using treatments with electro-generated oxygen. The application of chemometric techniques in this work highlighted the significance of the carbonyl and carboxylate spectral regions in the discrimination of cotton subjected to different levels of oxidative damage.

Polysaccharides

Various kinds of naturally occurring carbohydrate based polymers (oligosaccharides and polysaccharides) as well as artificially made (man-made) polymers based on various kinds of carbohydrate monomers, as well as chemically derived/modified naturally occurring or artificially made polysaccharides as well as co-polymers containing carbohydrate units can be oxidatively modified by means of a phenol oxidizing enzyme in combination with a suitable enhancing agent.

Based on this finding it is now possible to carry out chemical modification of oligo- or polysaccharides, fabric, yarn etc. containing soluble or insoluble polymer fibres, especially cellulosic fibres, by an enzymatic process in which a phenol oxidizing enzyme such as a peroxidase or a laccase, in combination with an enhancing agent, catalyzes the introduction of new functional groups in the oligo- or polysaccahride such as carbonyl groups and/or carboxylate groups.

Accordingly, the present invention provides a process for enzymatically oxidizing a soluble or an in-soluble oligo- or polysaccharide containing free hydroxy groups to carbonyl groups or carboxylate groups, wherein the soluble or in-soluble oligo- or polysaccharide is reacted with a phenol oxidizing enzyme in combination with an enhancing agent capable of catalyzing the oxidation.

The enzymatic oxidation according to the invention is normally a "mild" oxidation resulting in an oligo- or polysaccharide with an increased number of carbonyl and/or carboxylate groups, but with no or little ring openings. For most purposes ring openings and/or polymer scission are undesirably.

This enzymatically modified oligo- or polysaccharide is a good starting material for further modifications because carbonyl and carboxylate groups are reactive groups compared to hydroxy groups. Hereby textiles, fibres, yarns etc. with improved properties can be made. Examples of such properties are permanent press, softening, soil release, water repellancy and flame retardancy. The present invention provides a process by which, depending on the choice of conditions, (enzyme, enhancing agent, temperature, pH etc.) one or more of the desired properties may be obtained or improved in an easy, economical and environmentally friendly way. The wanted properties of the oligo- and polysaccharides will typically be achieved by further modifications, after the enzymatically oxidation according to the invention, by other means such as chemically and/or enzymatically modifications.

In the present specification and claims, the term "oligo- or polysaccharide"is intended to mean a polymeric material based on sugar monomers having hydroxy groups capable of being oxidized to carbonyl groups and/or carboxylate groups.

Of particular interest are oligosaccharides or polysaccharides based on the following sugars (monomers), either as homo-polymers (polymers based on a single monomer), or as hetero-polymers (polymers based on 2 or more different monomers):

Aldotetroses and ketotetroses such as erythrose and erythrulose;

aldopentoses such as arabinose, ribose, and xylose;

ketopentoses such as ribulose and xylulose;

aldohexoses such as glucose, galactose and mannose;

ketohexoses such as fructose and sorbose;

and sugar derivatives including deoxy-sugars such as deoxyribose, rhamnose and fucose, amino-sugars such as glucosamine and acidic carbohydrates such as glucuronic acid, galacturonic acid, mannuronic acid and guluronic acid.

Of further particular interest are naturally occurring carbohydrate polymers (oligo- and polysaccharides) as well as their products of hydrolysis, such as cellulose, hemicellulose, starch, xylan, xanthan gum, guar gum, gum arabic, Karaya gum, gellan gum, locust bean gum, konjak, curdlan, kappa carrageenan, alginates, agar-agar, pectins (high methoxyl, low methoxyl and amidated pectins and mixtures thereof), pectate, viscose, hydroxypropyl cellulose, chitin, schizophylan, chitosan, heparin, dextran, inulin, levan.

Preferably, the polysaccharide material subjected to the process of the invention is present as a fiber, a staple fiber such as a solvent-spun fiber, a filament, a thread, a yarn, or a textile fabric which may be woven, non-woven or knitted.

In a preferred embodiment of the invention, the polysaccharide is a cellulosic polymer fibre, i.e. containing cellulose or cellulose derivatives, preferably prepared from cotton, viscose (rayon), lyocell, flax (linen), ramie, or any blend thereof; and blends thereof with polyesters, wool, polyamides and (poly)acrylics. Typical examples of such blends are viscose/cotton, viscose/polyester, lyocell/polyester, lyocell/cotton, cotton/acrylic, cotton/polyester, cotton/polyester/acrylic, cotton/polyamide/polyester.

In yet another preferred embodiment of the invention, the polysaccharide is a synthetic polysaccharide based on sugar monomers, or chemically derived sugar monomers as well as copolymers of sugar monomers or polysaccharides and other polymer monomers or polymeric material.

Phenol Oxidizing Enzymes

Examples of suitable phenol oxidizing enzymes i.e. enzymes which act on aromatic compounds, in particular phenolic and/or polyphenolic compounds, are peroxidases (EC 1.11.1.7), laccases (EC 1.10.3.2), bilirubin oxidases (EC 1.3.3.5) monophenol monooxygenases (EC 1.14.18.1) and catechol oxidases (EC 1.10.3.1)

Peroxidases

Suitable peroxidases, according to the invention, may be any peroxidase enzyme comprised by the enzyme classification (EC 1.11.1.7), or any fragment derived therefrom, exhibiting peroxidase activity.

Preferably, the peroxidase employed in the method of the invention is producible by plants (e.g. horseradish or soybean peroxidase) or microorganisms such as fungi or bacteria. Some preferred fungi include strains belonging to the subdivision Deuteromycotina, class Hyphomycetes, e.g., Fusarium, Humicola, Tricoderma, Myrothecium, Verticillum, Arthromyces, Caldariomyces, Ulocladium, Embellisia, Cladosporium or Dreschlera, in particular Fusarium oxysporum (DSM 2672), *Humicola insolens*, Trichoderma resii, *Myrothecium verrucana* (IFO 6113), *Verticillum alboatrum, Verticillum dahlie,* Arthromyces ramosus (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g. Coprinus, Phanerochaete, Coriolus or Trametes, in particular *Coprinus cinereus* f. *microsporus* (IFO 8371), *Coprinus macrorhizus, Phanerochaete chrysosporium* (e.g. NA-12) or Trametes, e.g. T. versicolor, e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g., *Streptomyces spheroides* (ATTC 23965), *Streptomyces thermoviolaceus* (IFO 12382) or *Streptoverticillum verticillium* ssp. verticillium.

Other preferred bacteria include *Bacillus pumilus* (ATCC 12905), *Bacillus stearothermophilus, Rhodobacter sphaeroides*, Rhodomonas palustri, Streptococcus lactis, *Pseudomonas purrocinia* (ATCC 15958) or *Pseudomonas fluorescens* (NRRL B-11).

Further preferred bacteria include strains belonging to Myxococcus, e.g., *M. virescens*.

Particularly, a recombinantly produced peroxidase is preferred, e.g., a peroxidase derived from a Coprinus sp., in particular *C. macrorhizus* or *C. cinereus* according to WO 92/16634, or a variant thereof, e.g., a variant as described in WO 94/12621.

Laccases

Suitable laccase enzymes are known from microbial and plant origin. The microbial laccase enzyme may be derived from bacteria or fungi (including filamentous fungi and yeasts) and suitable examples include a laccase derivable from a strain of Aspergillus, Neurospora, e.g., *N. crassa*, Podospora, Botrytis, Collybia, Fomes, Lentinus, Pleurotus, Trametes, e.g., *T. villosa* and T. versicolor, Rhizoctonia, e.g., *R. sciani*, Coprinus, e.g. *C. plicatilis* and *C. cinereus*, Psatyrella, Myceliophthora, e.g. *M. thermophila*, Scytalidium, Polyporus, e.g., *P. pinsitus*, Phlebia, e.g., *P. radita* (WO 92/01046), or Coriolus, e.g., *C. hirsutus* (JP 2-238885), in particular laccases obtainable from Trametes, Myceliophthora, Scytalidium or Polyporus.

Phenol Oxidizing Enzyme Systems

If the phenol oxidizing enzyme requires a source of hydrogen peroxide, the source may be hydrogen peroxide or a hydrogen peroxide precursor for in situ production of hydrogen peroxide, e.g., percarbonate or perborate, or a hydrogen peroxide generating enzyme system, e.g. an oxidase and a substrate for the oxidase, or an amino acid oxidase and a suitable amino acid, or a peroxycarboxylic acid or a salt thereof. Hydrogen peroxide may be added at the beginning of or during the process, e.g. in a concentration corresponding to 0.001–25 mM $H_2O_2$.

If the phenol oxidizing enzyme requires molecular oxygen, molecular oxygen from the atmosphere will usually be present in sufficient quantity.

Enhancing Agents

In general any compound being substrate for a phenol oxidizing enzyme could be used as an enhancing agent. This includes aromatic compounds having functional groups like —OH, —NH, and —SH, in addition to heterocyclic compounds.

In particular the enhancing agent used in the present invention may be described by the following formula I:

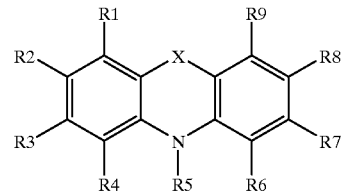

in which formula X represents (—O—) or (—S—), and the substituent groups $R^1$–$R^9$, which may be identical or different, independently represents any of the following radicals: hydrogen, halogen, hydroxy, formyl, carboxy, and esters and salts hereof, carbamoyl, sulfo, and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{10}$; and which phenyl may furthermore be unsubstituted or substituted with one or more substituent group's $R^{10}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{10}$;

which substituent group $R^{10}$ represents any of the following radicals: halogen, hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidino, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula two of the substituent groups $R^1$–$R^9$ may together form a group —B—, in which B represents any of the following the groups: (—CHR$^{10}$—N=N—), (—CH=CH—)$_n$, (—CH=N—)$_n$ or (—N=CR$^{10}$—NR$^{11}$—), in which groups n represents an integer of from 1 to 3, $R^{10}$ is a substituent group as defined above and $R^{11}$ is defined as $R^{10}$.

In particular embodiments, the enhancing agent is 10-methylphenothiazine, phenothiazine-10-propionic acid, N-hydroxysuccinimide phenothiazine-10-propionate, 10-ethyl-phenothiazine-4-carboxylic acid, 10-ethylphenothiazine, 10-propylphenothiazine, 10-isopropylphenothiazine, methyl phenothiazine-10-propionate, 10-phenylphenothiazine, 10-allylphenothiazine, 10-(3-(4-methylpiperazin-1-yl)propyl)phenothiazine, 10-(2-pyrrolidin-1-yl-ethyl)phenothiazine, 2-methoxy-10-methyl-phenothiazine, 1-methoxy-10-methylphenothiazine, 3-methoxy-10-methylphenothiazine, 3,10-dimethylphenothiazine, 3,7,10-trimethylphenothiazine, 10-(2-hydroxyethyl)phenothiazine, 10-(3-hydroxypropyl) phenothiazine, 3-(2-hydroxyethyl)-10-methyl-phenothiazine, 3-hydroxymethyl-10-methylphenothiazine, 3,7-dibromophenothiazine-10-propionic acid, phenothiazine-10-propionamide, chlorpromazine, 2-chloro-10-methylphenothiazine, 2-acetyl-10-methylphenothiazine, 10-methylphenoxazine, 10-ethyl-phenoxazine, phenoxazine-10-propionic acid, 10-(2-hydroxy-ethyl) phenoxazine or 4-carboxyphenoxazine-10-propionic acid.

The enhancing agent also may be described by the following formula II:

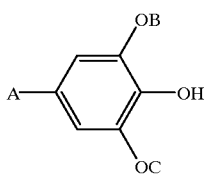

in which formula A is a group such as —D, —CH=CH—D, —CH=CH—CH=CH—D, —CH=N—D, —N=N—D, or —N=CH—D, in which D is selected from the group consisting of —CO—E, —SO$_2$—E, —N—XY, and —N$^+$—XYZ, in which E may be —H, —OH, —R, or —OR, and X and Y and Z may be identical or different and selected from —H and —R; R being a $C_1$–$C_{16}$ alkyl, preferably a $C_1$–$C_8$ alkyl, which alkyl may be saturated or unsaturated, branched or unbranched and optionally substituted with a carboxy, sulfo or amino group; and B and C may be the same or different and selected from $C_mH_{2m+1}$; 1 £ m £ 5.

In a preferred embodiment A in the above mentioned formula is —CO—E, in which E may be —H, —OH, —R, or —OR; R being a $C_1$–$C_{16}$ alkyl, preferably a $C_1$–$C_8$ alkyl, which alkyl may be saturated or unsaturated, branched or unbranched and optionally substituted with a carboxy, sulfo or amino group; and B and C may be the same or different and selected from $C_mH_{2m+1}$; 1 £ m £ 5.

In the above mentioned formula A may be placed meta to the hydroxy group instead of being placed in the paraposition as shown.

In particular embodiments, the enhancing agent is acetosyringone, methylsyringate, ethylsyringate, propylsyringate, butylsyringate, hexylsyringate, or octylsyringate.

The enhancing agent may also be one of the enhancing agents described in WO 91/05839 such as pHBS, pHBA, Vanillin, Coumaric acid, or Cinnamic acid.

The enhancing agent may also be one of the compounds disclosed in WO 96/18770 such as N-hydroxy compounds, in particular aliphatic, cycloaliphatic, heterocyclic or aromatic compounds containing NO—, N(OH)—, or N(OH) ($R_1$), especially N-hydroxy benzotriazol (HOBT), Violuric acid, or N-hydroxyacetanilide (HAA).

In a preferred embodiment of the invention the mediator is a compound of the general formula III:

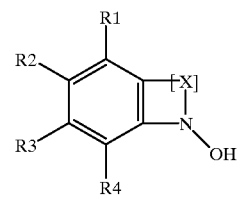

wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof,

[X] represents a group from (—N=N—), (—N=CR$^6$—)$_m$, (—CR$^6$=N—)$_m$, (—CR$^7$=CR$^8$—)$_m$, and m is 1 or 2.

In a more preferred embodiment of the invention the mediator is a compound of the general formula IV:

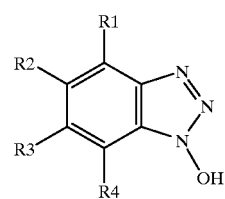

wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof.

The mediator may also be a salt or an ester of formula III or IV.

Further preferred mediators are oxoderivatives and N-hydroxy derivatives of heterocyclic compounds and oximes of oxo- and formyl-derivatives of heterocyclic compounds, said heterocyclic compounds including five-membered nitrogen-containing heterocycles, in particular pyrrol, pyrazole and imidazole and their hydrogenated counterparts (e.g. pyrrolidine) as well as triazoles, such as 1,2,4-triazole; six-membered nitrogen-containing heterocycles, in particular mono-, di- and triazinanes (such as piperidine and piperazine), morpholine and their unsaturated counterparts (e.g. pyridine and pyrimidine); and condensed heterocycles containing the above heterocycles as substructures, e.g. indole, benzothiazole, quinoline and benzoazepine.

Examples of preferred mediators from these classes of compounds are pyridine aldoximes; N-hydroxypyrrolidinediones such as N-hydroxysuccinimide and N-hydroxyphthalimide; 3,4-dihydro-3-hydroxybenzo[1, 2,3]triazine-4-one; formaldoxime trimer (N,N',N"-trihydroxy-1,3,5-triazinane); and violuric acid (1,3-diazinane-2,4,5,6-tetrone-5-oxime).

Still further mediators which may be applied in the invention include oximes of oxo- and formyl-derivatives of aromatic compounds, such as benzoquinone dioxime and salicylaldoxime (2-hydroxybenzaldehyde oxime), and N-hydroxyamides and N-hydroxyanilides, such as N-hydroxyacetanilide.

Preferred mediators are selected from the group consisting of 1-hydroxybenzotriazole; 1-hydroxybenzotriazole hydrate; 1-hydroxybenzotriazole sodium salt; 1-hydroxybenzotriazole potassium salt; 1-hydroxybenzotriazole lithium salt; 1-hydroxybenzotriazole ammonium salt; 1-hydroxybenzotriazole calcium salt; 1-hydroxybenzotriazole magnesium salt; and 1-hydroxybenzotriazole-6-sulphonic acid.

A particularly preferred mediator is 1-hydroxybenzotriazole.

All the specifications of N-hydroxy compounds above are understood to include tautomeric forms such as N-oxides whenever relevant.

In particular, the enhancing agent of the invention may be the corresponding N-oxyl free radical to any of the compounds disclosed in WO 96/18770 such as TEMPO (2,2,6, 6-tetramethylpiperidinoxyl).

Industrial Applications

The oligo- or polysaccharide may be processed in aqueous medium, although other media/solvents might be added at various concentrations, e.g., detergents, tensides, lubricants, organic solvents, silicone oils, mineral oils, and/or vegetable oils. Typically a liqour:oligo-or polysaccharide ratio in the range of from 1:1–20:1 will be used, and typically the treatment will be made at a temperature in the range of from 10° C.–150° C., preferably in the range of from 40° C.–80° C. The process will typically be run for 5–120 minutes. Typical dosages of enzyme will be 0.01–100 μg enzyme protein/g oligo-or polysaccharide, and typical dosages of enhancing agents, if added, will be in the range 0.01–100 μmole/g oligo- or polysaccharide.

Evaluation of the Oxidative Treatment:

As mentioned earlier the enzymatic treatment according to the invention may be evaluated by means of vibrational spectroscopic techniques such as FTIR, DRIFT, or FTIR-PAS although other spectroscopic techniques as well as other techniques might be used. By such techniques it will be possible to evaluate the degree of oxidation obtained as well as the molecular nature of the oxidative changes introduced in the oligo-/polysaccharide. Preferably the spectroscopic techniques may be combined with multivariate analysis (chemometrics) for detailed data analysis as described in the previous sections, preferably concentrating the data analysis to the wavenumber range 1800 $cm^{-1}$–800 $cm^{-1}$ and in particular the wavenumber range 1800 $cm^{-1}$–1500 $cm^{-1}$ as this range in particular reflects typical oxidation products formed.

The present invention is further illustrated in the following example which is not in any way intended to limit the scope of the invention as claimed.

EXAMPLE 1

Cotton Cellulose:

Un-dyed and un-bleached 100% cotton twill, 195 g/m² (obtained from Grenaa Dampveveri A/S, Oesterbrogade 45, DK-8500 Grenaa). Prior to use the fabric was desized with Aquazym Ultra 1200 (obtainable from Novo Nordisk A/S) as per the manufacturers instructions. Following desizing, the fabric was tumble dried. The fabric was cut into pieces of approximately 6 g each (approximately 12×24 cm each).

Enzyme:

Trametes villosa lacase (TvL) (previously called Polyporus pinsitus laccase) (obtainable from Novo Nordisk A/S).

Mediator:

TEMPO (2,2,6,6-Tetramethyl-1-piperidinyloxy free radical) (Fluka cat# 87903).

Processing:

To a 1200 ml total volume stainless steel LOM beaker was added: 4×6 g fabric, 240 ml buffer (0.75 g/L $KH_2PO_4$ adjusted to pH 6), 4.7 mg TvL, 0.015 g TEMPO. The LOM beaker was tightly capped and placed in the launder-o-meter (Atlas LP2 Launder-o-meter) and processed at 60° C. for 30 minutes. Following processing the fabric was rinsed in de-mineralised water three times and dried.

Evaluation by Vibrational Spectroscopy Techniques:

Sample Preparation and Spectroscopic Aspects:

Circular pieces (ca. 6 mm diameter) were cut from each sample of fabric and were pre-conditioned to certain humidity (65 R.H.) and temperature 22° C. in a microprocessor temperature controller (Clayson IM1000R Incubator) for one week prior to any experimental work.

For the FT-IR/PAS experiments single circular pieces were placed into a sample cup (6 mm) and then placed into the Photoacoustic accessory (MTEC Model 200).

A Perkin-Elmer 2000 FT-IR spectrometer was used for the infrared studies. Carbon black was used as a reference material and prior to collecting spectra the cell was purged with helium for 10 minutes. Spectra were collected over the entire range (4000–450 $cm^{-1}$). A spectral resolution of 8 $cm^{-1}$, 128 scans and a mirror velocity of 0.2 cm/s were employed. The spectra were collected under normal laboratory conditions (22° C.).

FT-IR/PAS spectra of untreated white cotton as well as white cotton treated with Tempo/TvL covering the range 1800–1500 $cm^{-1}$ is shown in FIG. 1.

From FIG. 1 it is obvious, that the content of carbonyl groups has increased as a result of the Tempo/TvL treatment (denoted "TEMPO" in FIG. 1) as the intensity of the peaks at 1714 $cm^{-1}$ and especially 1734 $cm^{-1}$ has increased [Yang, C. Q. (1991), Appl. Spectrosc., 45(1), pp 102–108].

What is claimed is:

1. A process for oxidation of $C_1$ and/or $C_2$ and/or $C_3$ and/or $C_4$ and/or $C_5$ and/or $C_6$ hydroxy group of a sugar monomer of a starch comprising contacting, in an aqueous medium, the starch with a peroxidase together with a hydrogen peroxide source and an enhancing agent, in which said oxidation results in formation of a carbonyl or carboxylate group.

2. The process according to claim 1, wherein said oxidation is of the $C_6$ hydroxy group.

3. The process according to claim 1, wherein the peroxidase is horseradish peroxidase, soybean peroxidase or a peroxidase enzyme obtainable from Coprinus, Bacillus, or Myxococcus.

4. The process according to claim 1, wherein the hydrogen peroxide source is hydrogen peroxide, a hydrogen peroxide precursor, a hydrogen peroxide generating enzyme system, or a peroxycarboxylic acid or a salt thereof.

5. The process according to claim 4, wherein the aqueous medium contains $H_2O_2$ or a precursor for $H_2O_2$ in a concentration corresponding to 0.001–25 mM $H_2O_2$.

6. The process according to claim 1, wherein the concentration of the peroxidase corresponds to 0.01–100 mg of enzyme protein per g of starch.

7. The process according to claim 1, wherein the enhancing agent in the aqueous medium is present in concentrations of from 0.01 to 100 mmole per g of starch.

8. The process according to claim 1, wherein the aqueous medium comprises an enhancing agent which is selected from the group consisting of aliphatic, cycloaliphatic, heterocyclic or aromatic compounds containing NO—, N(OH)—, N(OH)R, or the corresponding N-oxyl free radicals thereof.

9. The process according to claim 8, wherein the enhancing agent is a compound of formula:

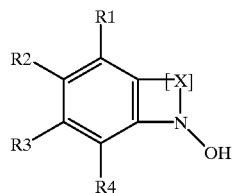

wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof, [X] represents a group from (—N=N—), (—N=CR$^6$—)$_m$, (—CR$^6$=N—)$_m$, (—CR$^7$=CR$^8$—)$_m$, and m is 1 or 2.

10. The process according to claim 8, wherein the enhancing agent is a compound of formula:

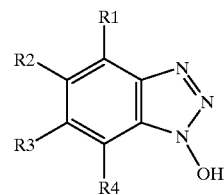

wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl), aryl, in particular phenyl, sulfo, aminosulfonyl, carbamoyl, phosphono, phosphonooxy, and salts and esters thereof.

11. The process according to claim 8, wherein the enhancing agent is selected from the group consisting of N-hydroxybenzotriazole, violuric acid, N-hydroxyacetanilide and TEMPO.

* * * * *